(12) United States Patent
Petcu et al.

(10) Patent No.: US 7,229,836 B2
(45) Date of Patent: Jun. 12, 2007

(54) POLYMERS FOR BINDING OF PHENOLS

(75) Inventors: Miruna Petcu, Hamilton (NZ); Janine Cooney, Hamilton (NZ); Christian Cook, Hamilton (NZ); Denis Lauren, Hamilton (NZ)

(73) Assignee: The Horticulture and Food Research Institute of New Zealand Limited, Hamilton (NZ)

( * ) Notice: Subject to any disclaimer, the term of this patent is extended or adjusted under 35 U.S.C. 154(b) by 232 days.

(21) Appl. No.: 10/311,328

(22) PCT Filed: Jun. 29, 2001

(86) PCT No.: PCT/NZ01/00128

§ 371 (c)(1),
(2), (4) Date: Jun. 25, 2003

(87) PCT Pub. No.: WO02/00737

PCT Pub. Date: Jan. 3, 2002

(65) Prior Publication Data

US 2004/0096979 A1     May 20, 2004

(30) Foreign Application Priority Data

Jun. 30, 2000  (NZ) ................................. 505525

(51) Int. Cl.
*G01N 33/00*    (2006.01)
(52) U.S. Cl. .................................... 436/127; 525/330.3
(58) Field of Classification Search ................. 436/127
See application file for complete search history.

(56) References Cited

U.S. PATENT DOCUMENTS

| | | | |
|---|---|---|---|
| 4,069,105 A | 1/1978 | Singh | 195/63 |
| 4,650,771 A | 3/1987 | Buckler et al. | 436/536 |
| 5,110,833 A | 5/1992 | Mosbach | 521/50 |
| 5,630,978 A | 5/1997 | Domb | 264/330 |
| 5,858,296 A | 1/1999 | Domb | 264/330 |
| 6,057,377 A | 5/2000 | Sasaki et al. | 521/99 |
| 6,063,637 A | 5/2000 | Arnold et al. | 436/94 |
| 6,447,764 B1 * | 9/2002 | Bayer et al. | 424/78.1 |

FOREIGN PATENT DOCUMENTS

| | | |
|---|---|---|
| EP | 0925776 A2 | 6/1999 |
| GB | 2337332 A | 11/1999 |
| WO | WO99/65528 | 12/1999 |

OTHER PUBLICATIONS

Masque et al, Anal. Chem. 72, 2000, pp. 4122-4126, Synthesis and Evaluation of a Molecularly Imprinted Polymer for . . . .
Joshi et al, Chem Eng Sci. 55, 2000, pp. 1509-1522, Enhancing adsorptive separations by molecularly imprinted polymers: . . . .
Joshi et al, Chem Eng Sci. vol. 53, No. 13, 1998, pp. 2271-2284 Novel separation strategies based on molecularly imprinted . . . .
Haginaka et al, CHEMISTRY LTRS. 1999, pp. 757-758, Uniform-sized Molecularly Imprinted Polymers for Bisphenol A.
Haginaka et al, Chemical Abstract Accession No. 2000:7482, vol. 132, Preparation of molecularly imprinted polymers for . . . .
Perez et al, J. Appl. Polym. Sci., vol. 77, No. 8, 2000, pp. 1851-1859, Molecularly Imprinted Nanoparticles Prepared by . . . .
Wulff, Angew. Chem. Int. Ed. Engl. 34, 1995, pp. 1812-1832, Molecular Imprinting in Cross-Linked Materials with the Aid . . . .
Brimble et al, Tetrahedron: Asymmetry 9, 1998, pp. 873-884, Asymmetric azo-ene reactions using the chiral azo-enophile . . . .
Whitcombe et al, J. Am. Chem. Soc., 117, 1995, pp. 7105-7111, A New Method for the Introduction of Recognition Site . . . .
Corson et al, Corson, Heintzelman et al, vol. 23, pp. 544-549, Preparation of Vinylphenols and Isopropenylphenols.

* cited by examiner

*Primary Examiner*—Robert D. Harlan
(74) *Attorney, Agent, or Firm*—Jacobson Holman PLLC

(57) ABSTRACT

The invention relates to a method for the detection and/or measurement of a phenol comprising: (a) contacting the sample to be tested with a polymer imprinted with the phenol or an analogue thereof; and (b) measuring binding of the phenol to the polymer. The polymer may be prepared by polymerizing a polymerizable monomer, to which a phenol is covalently bound by a hydrolysable linker, and subsequently removing the phenol by hydrolysis. Propofol is a preferred phenol for use in the invention.

25 Claims, 4 Drawing Sheets

Figure 2
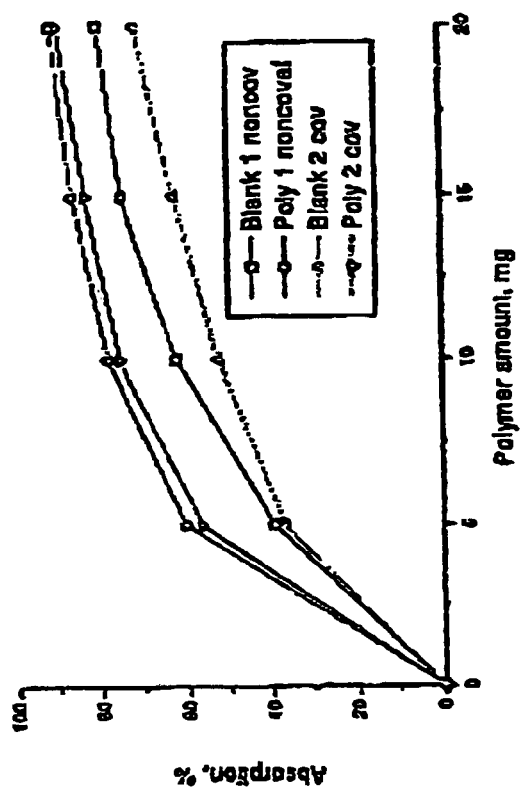
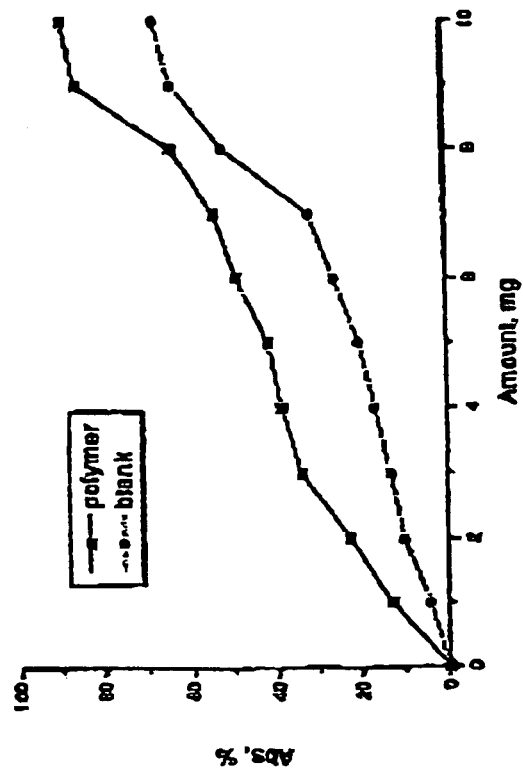

POLYMERS FOR BINDING OF PHENOLS

This is a nationalization of PCT/NZ01/00128 filed Jun. 29, 2001 and published in English.

TECHNICAL FIELD

This invention relates to the binding of phenols to polymers and applications thereof.

BACKGROUND

Anaesthesia, and particularly general anaesthesia, is a high risk form of treatment for a patient. The rate of metabolism of an anaesthetic in individuals varies widely, as does the level of effectiveness. Patient safety requires that they be continuously observed for signs of distress and levels of consciousness. It is also desirable, for a given individual patient, to be able to establish the level of anaesthetic effectiveness, the rate at which this is achieved and the anaesthetic dosage level required to maintain an appropriate level of unconsciousness. Patient care can therefore be optimised by minimising side effects and recovery time, and maximising anaesthetic effectiveness.

For optimised patient care, a rapid and specific analytical method is needed for measuring concentrations of anaesthetics in biological fluids, as distinct from closely related compounds. This need has led to the development of a variety of procedures for monitoring both levels of consciousness in patients and levels of anaesthetic in blood or plasma.

Patient monitoring techniques generally comprise physical monitoring of indicators such as heart rate, blood pressure and eye flicker. EEG monitoring is also feasible.

Anaesthesia monitoring generally relies on measurement of expiration gases, or more recently high performance liquid chromatography (HPLC) or ELISA for analytes in biological fluid samples.

Some twenty years ago U.S. Pat. No. 4,069,105 disclosed enzyme immunoassays for measuring levels of anaesthetics involving anilides, lidocaine being illustrative. The anaesthetics described therein were generally formulated for administration other than intravenously, with assays being carried out on samples removed from the patient.

The anaesthetic derivatives therein comprised anilide functionality drugs, linked via an annular amino substituent to antigens to produce an antigenic conjugate. In turn, the antigenic conjugate was used for the production of antibodies to the subject drug, and for use in immunoassays.

In U.S. Pat. No. 4,650,771 in 1983, the art was further developed by providing anilide derivative anaesthetics conjugated to antigens via one of the aromatic methyl substituents. Immunoassays on fluid samples were again proposed.

In 15 to 20 years which followed the publication of these U.S. patents, there have been many developments in the field of anaesthesia. Currently preferred anaesthetics are formulated for intravenous or intramuscular administration and include phenol derivative anaesthetics such as propofol. Propofol, commonly known as Diprivan is a fast acting anaesthetic commonly intravenously administered in medial anaesthesia. The existence of this preferred anaesthetic has been know for tens of years.

While this anaesthetic can be measured using HPLC methods, there are currently no methods to measure the concentration of the intravenous/intramuscular anaesthetics in patients in real-time, on-line or with easy convenience in a clinical setting. Moreover, no known antibody detection methods to these types of anaesthetics are in clinical use. As the mechanism of action of these anaesthetics are also poorly understood, the development of binding materials for these anaesthetics to enable rapid and clinically relevant detection methods using kits or off-line or in real-time biosensors would therefore fulfill a long felt want.

Other phenols are important in medicine, industry and as environmental contaminants. Improved convenient assays for these compounds are likewise desirable.

It is an object of this invention to provide new binding materials for use in detection of phenols and biosensors and/or methods which go some way to addressing the aforegoing or at least provide the public with a useful choice.

DISCLOSURE OF THE INVENTION

According to one aspect of the present invention there is provided a method for the detection and/or measurement of a phenol comprising
  a) contacting the sample to be tested with a polymer imprinted with the phenol or an analogue thereof,
  b) measuring binding of the phenol to the polymer.

In another aspect the invention provides a polymer which binds a phenol wherein said polymer has been imprinted with the phenol or an analogue thereof.

In another aspect the invention provides a polymer containing covalently bound or a noncovalently bound phenol which can be removed to yield an imprinted polymer.

The phenol may be phenol itself or a substituted phenol with a single six-membered ring. The ring may be mono- di- or trisubstituted. Preferred substituents include $C_1$–$C_6$ alkyl, halogen, $C_1$–$C_6$ alkoxy, $C_1$–$C_6$ alkylthio, amino, $C_1$–$C_6$ alkylamino, di($C_1$–$C_3$ alkyl) amino, —$CONH_2$, —CN, carboxy, hydroxy, $C_1$–$C_6$ alkylsulfonyl, nitro, and substituted $C_1$–$C_6$ alkyl or alkoxy wherein the substituent is selected from halogen, hydroxy, $C_1$-$C_3$ alkoxy, amino, —$CONH_2$, —CN and carboxy. Preferably the substituents are $C_1$–$C_3$ alkyl groups.

Preferred phenols for use in the invention are cresols and propofol, especially propofol.

In a preferred embodiment of the invention there is provided a method for the detection and/or measurement of propofol comprising
  a) contacting the sample to be tested with a polymer imprinted with propofol or an analogue thereof,
  b) measuring binding of propofol to the polymer.

In another preferred embodiment, the invention provides a polymer which binds propofol wherein said polymer has been imprinted with propofol or an analogue thereof.

In another preferred embodiment, the invention provides a polymer containing a covalently bound or noncovalently bound propofol which can be removed to yield an imprinted polymer.

Preferred sample materials include biological fluid such as blood, plasma and serum.

The binding of the phenol to the polymer may be detected in a variety of ways. For example the imprinted polymer may be used in an assay corresponding to a radioimmunoassay whereby the polymer replaces antibody or is used in a biosensor with either optical or electrochemical detection.

Imprinted polymer membranes may be used as the basis of chemosensors. Such chemosensors may take the form of an ion selective electrode.

The imprinted polymers according to the invention can be prepared in a variety of ways. The common feature is that a phenol is incorporated during the polymerisation process and then later removed. The phenol may be bound covalently. Alternatively it may be bound non-covalently. The phenol may be bound to a polymerisable monomer through a hydrolysable linker. This allows hydrolysis of the linker after polymer formation to release the profofol leaving the imprinted polymer. A variety of types of groups can be used to link the propofol to the polymer. These are well known in the art see G Wulff *Angew. Chem. Int. Ed. Engl.* (1995) 34, 1812–1832 and include boronic acid ester groups, Schiff base, ketals, acetals and chelate complexes. Amide and ester links may also be used but are not preferred as removal of the imprinting material is difficult.

Particularly preferred is use of carbonate esters which can be efficiently cleaved hydrolytically with a loss of $CO_2$. The resulting binding site phenol is capable of interacting with an alcohol through hydrogen bonding.

Preferred for use in the invention are covalently imprinted polymers formed by polymerising a monomer of formula MXP wherein P is a phenoxy group, for example a 2,6-diisopropylphenoxy group.

M is a polymerisable group preferably containing an alkenyl group, more preferably a propenyl or vinyl group.

Most preferably M is a vinylphenoxy group.

X is a linker group or a bond susceptible to hydrolysis. X or the X-M bond or the X-P bond may be cleaved under conditions which do not result in destruction of the backbone of the polymer to be formed. Preferably X (or X together with M and/or P) forms a boronic acid ester group, a ketal, an acetal or a —O—CO—O— group, most preferably a —O—CO—O— group.

Non-covalent interactions can also be used. The polymer is formed by adding the imprinting phenol during formation or crosslinking of the polymer. The polymer is selected to there will be electrostatic interaction, hydrogen bond formation or hydrophobic interactions with the phenol creating binding sites for he phenol.

Preferred noncovalent polymers include crosslinked polyacrylates and polymethyacrylates, preferably crosslinked polymethyacrylates. The preferred crosslinker is ethylenedimethacrylate. Preferably the ratio of comonomer to crosslinker is in the ratio 1:1 to 1:15 most preferably 1:4 to 1:15.

In preferred embodiments of the invention the polymer to be used in the assay is ground repeatedly to reduce non-specific binding. Preferably the particle size of at least 50% by weight of the polymer is in the range 0.5–5 microns. More preferably more than 80% of the material consists of particles in that size range.

The above described polymers may be used in assays which are analogous to radioimmunoassays. For example the radiolabelled phenol (for example [$C^{14}$] propofol) may be incorporated into a sample. Binding of the radioactive phenol to the polymer will be inversely related to the amount of relevant phenol present in the sample. The binding of the phenol may be determined after separating the polymer from the liquid medium. This may conveniently be achieved by centrifugation.

Another method for analysing propofol involves incorporation of the polymer into a biosensor.

A preferred biosensor comprises an amperometric probe with an electrode, preferably molecularly imprinted polymer (MIP) coated platinum mesh. A reference probe is incorporated according to standard design techniques. Reference electrode materials include silver, gold, platinum or stainless steel. Preferred electrodes are Ag, Ag/AgCl combination. The electrodes may be connected to external points.

The probe assembly is fitted within a body or housing to form an indicator probe. Such probes are exemplified in Examples 7 and 8.

In a preferred embodiment op the invention, the imprinted polymer is formed by placing the polymerisation mixture on a porous polymer membrane such as PTFE membrane with a 0.5 micron cutoff and allowed to polymerise. The resultant membrane can be used in biosensor.

In another aspect of the invention the phenol is propofol and its concentration during anaesthesia is monitored using an assay based on binding of propofol onto a polymer previously imprinted with propofol, either by optical or electrochemical detection.

Certain preferred aspects of the invention will now be described in relation to the following non-limiting examples.

BRIEF DESCRIPTION OF THE DRAWINGS

FIG. 2 shows percentage absorption plotted against amount of propofol.

EXAMPLE 1

Covalently Imprinted Polymer

Figure 1:
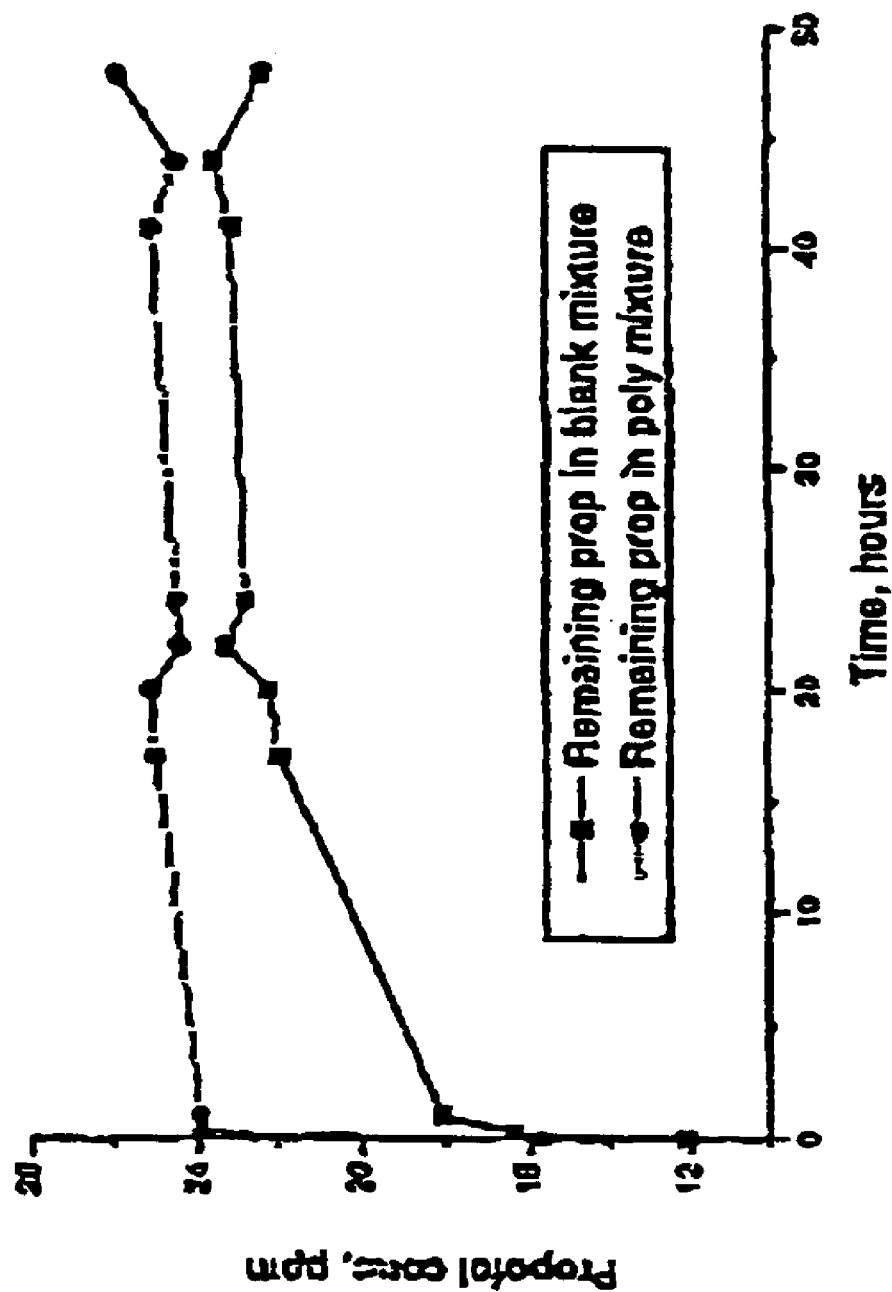
FIG. 1 shows binding of propofol to imprinted polymer and control polymer over time.

The Synthesis of the Monomer Illustrated in Reaction Scheme I

1. Chloroformate synthesis

REACTION SCHEME I

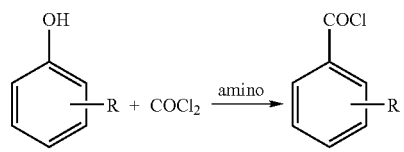

Phenol: phosgene: amine 1:3: 1.1
Reaction under N2; TLC monitored
Reaction time between 4 and 48 hours
Product used as it is, after removal of excess phosgene;
NMR characterisation, purity>95%

2. Vinylphenol synthesis

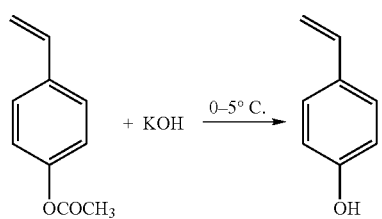

needed recrystallization from boiling hexane
NMR characterisation, 99.5% pur

3. Monomer synthesis

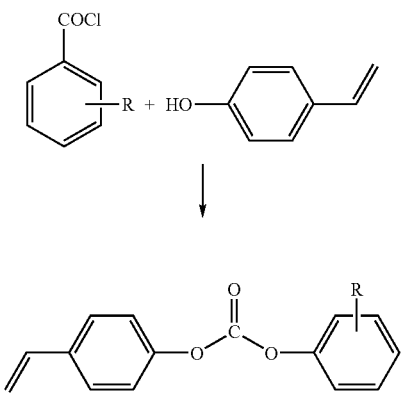

Column purification NMR characterisation, used when purity at least 98%

1.1 Preparation of 2,6 diisopropylbenzoylchloride

The reaction is based on that described by Brimble and Lee in *Tetrahedron: Asymmetry* 9 (1998) 873–844. Molar ratios used were propofol: phosgene:amine 1:3:1.1. The phosgene (12.5% solution in toluene) was put in a flash immersed in an ice bath and the propofol and diisopropylethylamine was added dropwise over 15 minutes, the flask was allowed to get to room temperature and the reaction was monitored by TLC (60–40 cyclohexane-dichloromethane) until all propofol disappeared, the chloroformate was NMR characterised and used for reaction No. 3 without further purification. The reaction time was approx 48 hours.

1.2 Preparation of 4-vinylphenol

The reaction is based on that described by Corson et al. J Org Chem (1958) 544–549; molar ratios acetoxystyrene: base 1:1.5. The base, KOH in water (30%) was immersed in an ice bath and the acetoxystyrene was added dropwise over 30 mins (all reaction carried under $N_2$; the reaction was TLC monitored (20–80 cyclohexane-dichloromethane) until all acetoxystyrene disappeared, then the pH was brought down to 8 with $CO_2$; the resulting precipitate was filtered and washed with water, then recrystallised from boiling hexane and NMR characterised.

1.3 Preparation of Monomer (2,6-diisopropyl)phenyl (4-vinyl)phenyl carbonate.

The reaction is based on that described by Whitcombe et al (J Am Chem Soc 117, 7105–7111 (1995)); the molar ratios were choroformate:vinylphenol: diisopropylethylamine 1:1.2. The vinylphenol was dissolved in dry THF and the base added; the flask was kept in an ice bath an the chlorformate added dropwise; the flask was allowed to get to room temperature and the reaction was monitored (TLC 60–40 cyclohexane-dichloromethane)), the solvent was removed and the raw mixture was dissolved in $CH_2Cl_2$. After extraction with water the organic layer was taken down to dryness and the monomer was separated by purification on a silica column using a stepwise gradient of $CH_2Cl_2$-hexane (from 5% $CH_2Cl_2$ to 80%). The analysis showed purity >98%. The overall reaction scheme for preparation of them monomer is illustrated in Reaction Scheme I.

1.4 Polymerisation and Removal of Propofol

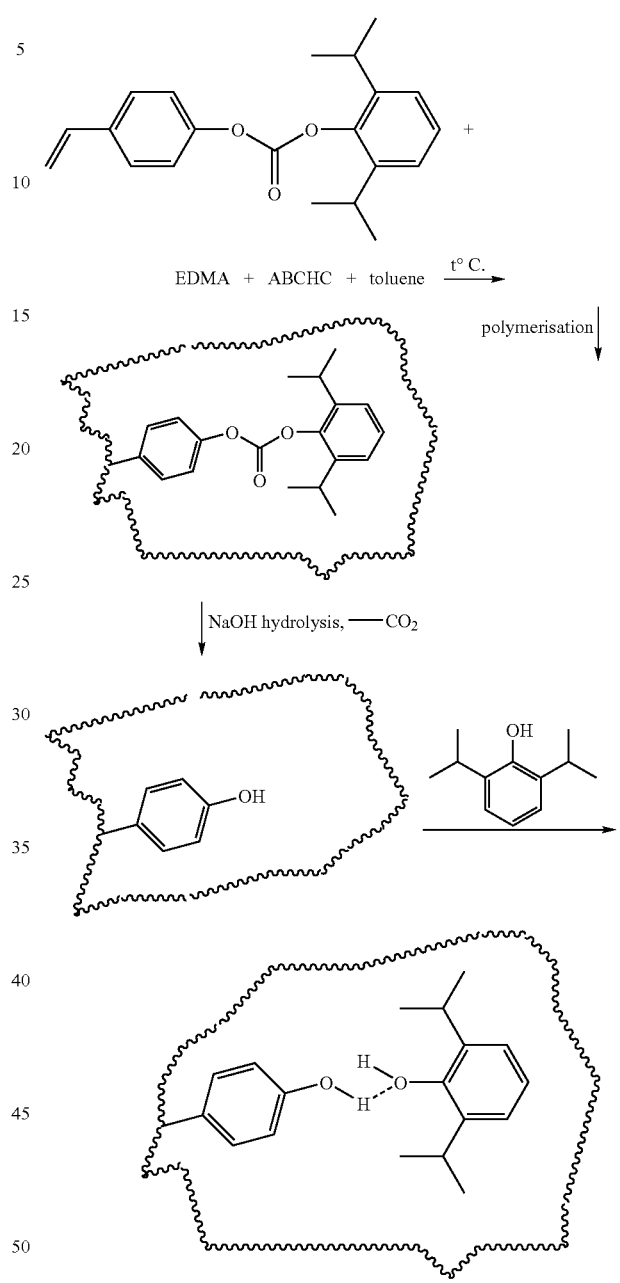

The polymerisation carried in a manner similar to that Whitcombe et al. The Molar ratio used was of (2,6-diisopropyl)phenyl (4-vinylphenyl) carbonate to crosslinker (ethylenedimethacrylic acid) to 1,1'-azobis(cyclohexanecarbonitrile) (ABCHC) was 1:19:0.125 for bulk and 1:1:0.125 for membranes, 2 ml/g monomers as porogen (toluene). The polymerisation took 48 hors to complete at 60–80° C. for bulk polymer and 24 hours for the membranes.

The bulk polymer (brittle solid) and the blank (everything but the monomer) were grinded for 75' at 30 $s^{-1}$, then refluxed for 6 hours in NaOH 1 M in $CH_3OH$; after neutralisation with a slight excess of HCl (dilute), they were washed with water, methanol and ether.

After drying in air for 24 hours—Soxblet extraction with methanol for 18 hours and hexane for 8 hours, the polymers were allowed to air dry before being subjected to tests.

1.5 Binding Tests

Batch binding tests were carried out by allowing the polymer contact with propofol solutions (0.2 mM and 2 mM solutions in methanol). After centrifugation, the supernatant was analysed (HPLC 60–40 $CH_3CN$—$H_2O$) and the binding was assessed.

Initially the binding was 89% in imprinted polymer, 78% in blank polymer in 0.2 mM, 73% in imprinted polymer, 54% in blank polymer in 2 mM.

The nonspecific binding (defined as the absorption in he blank polymer) was high and we assumed this is because the particles were too big. After further grinding (total of 2 h at $305^{-1}$) the abs was 18% for imprinted polymer, 3% blank polymer in 0.2 mM, 12% imprinted polymer, 3% blank polymer in 2 mM.

For the membranes, the imprinted and non-imprinted membranes were allowed to come in contact for 2 min (time determined by studying the kinetics of the binding) with a known-concentration propofol solution. The remaining propofol in solution after the test was analysed by HPLC and this was double-checked by an optical analysis.

After rinsing with water, the membrane was allowed to come in contact with a 1:1 mixture of methanol-bicarbonate buffer pH 9.6. After one minute, the contact solution was made to react with Gibbs reagent 0.5 mM in methanol (2 parts bicarb mixture to 1 part Gibbs) and the colour (varying from yellow to blue, depending on concentration) read at 594 nm.

EXAMPLE 2

Non-Covalently Imprinted Polymer

This polymerisation involved polymerising methacrylic acid (MAA) using ethylenedimethylacrylic acid (EDMA). The ratios used to prepare a propofol imprinted polymer were propofol:MAA:EDMA:initiator ABCHC (a) 1:4:30:0.17: (1.65 ml/g in porogen (hexane))

(b) 1:4:25:0.125 (2 ml/g in hexane).

Blank polymer is as prepared in the same way but with omission of propofol.

The solution was thermally polymerised (60–80° C.) for 24 hours.

After grinding and extracting with methanol-hexane-batch binding tests were performed by allowing the polymer to come in contact with solutions (0.2 m and 2 m propofol solution in methanol). After centrifugation, the supernatant was analysed (HPLC, 60–40 $CH_3CN$—$H_2O$) and the binding was assessed. For both polymers we have also done the corresponding blanks (everything but the template).

Absorption (binding) was (a) 87% in imprinted polymer, 66% in blank polymer from 0.2 64% in imprinted polymer, 28% in blank polymer from 2

(b) 67% in imprinted polymer, 66% in blank polymer from 0.2 26% in imprinted polymer, 31% in blank polymer from 2

These results showed high non specific binding (that is binding by the blank polymer). However imprinted polymer (a) showed higher binding than its blank polymer.

EXAMPLE 3

Tests against other phenols

W tested the covalently imprinted polymer of Example I and the noncovalently imprinted polymer (a) of Example 2 against m-cresol. The tests were done;

1. Only with m-cresol solution

The batch binding was performed as before the absorptions were:

Covalent—0 in both imprinted and blank polymers;

Noncovalent—0 in blank polymer, 7% in imprinted polymer;

2. With a mixture of propofol and m-cresol.

The Percentage Absorptions Were:

Covalent—(94% propofol 63%/m-cresol) blank polymer; (100% propofol and 76% m-cresol) imprinted polymer Noncovalent—(91% propofol-47%/m-cresol) blank; (94% propofol and 46% m-cresol) imprinted polymer;

The tests were performed with the polymer coarsely grinded. This leads to higher non specific binding but the results show preferential binding of propofol to the imprinted polymer.

EXAMPLE 4

Effect of Grinding

The covalent polymers made for propofol (following Example 1) were cleaned and extracted. The blank and polymer were ground for 15 min at 30 Hz. This was considered initial grinding.

All the batch binding experiments are made following the same pattern: 20 mg of polymer or blank (by blank meaning nonimprinted polymer) are shaken for 15 minutes with a 0.2 mM solution of propofol in methanol, then centrifuged at 2500 rpm for 5 min, he supernatant is removed and analysed (HPLC) for he amount of propofol left in solution.

The polymers thus ground and cleaned are tested against propofol and this gives our initial values of 36.4% specific binding and 41.25% nonspecific binding.

The polymers are given another batch of grinding (another 15 min, same frequency) and the subsequent test shows 36.73% specific and 35.83% nonspecific.

After another 30 min grinding at the same frequency, they were tested. The results were: 17.66% specific and 2.62% nonspecific. The polymers had a last batch of grinding (15 min). The last batch binding test shows a 10.77% specific and a 2.57% nonspecific binding. At this point the experiment was stopped because the nonspecific binding was not decreasing anymore, and the specific binding was going too low.

The nonspecific and the specific binding are decreasing with decreasing particle size (the final particle sizes are mostly between 0.5 and 5 microns). But by the time the nonspecific biding gets to 2–3% (so practically very close to 0) the nonspecific is still 18% and thus can serve in a biosensor system for a very accurate separation-measurement. The last-step-grinding polymer against o- and m-cresol, very similar in structure with propofol, and o-cresol has 0% binding, m-cresol has 2.9% binding. These values are not going to interfere with a binding of propofol biosensor.

EXAMPLE 5

Variation of Binding with Time, Amount of Polymer

FIG. 1 shows binding of propofol with time. The ratio of binding to the imprinted polymer (poly) relative to the control polymer (blank) is greatest in the first 15 mins. The polymer was allowed to come in contact with the same amount of solution for different amounts of time and the binding was assessed after specific times. The experiment followed the batch binding experiment described in Example 4 (all batch binding experiments follow the same routine). 20 mg of polymer were shaken for different set times (see FIG. 1) with a 0.2 mM propofol solution in methanol-2 mL, then after removal of particles by centrifugation at 2500 rpm for 5 min, the remaining propofol in solution was assessed by HPLC.

FIG. 2 shows binding of propofol increases with the amount of polymer present. This applies to binding to imprinted polymer (a) of Example 2 (Poly 1 noncoval), the corresponding non imprinted polymer (Blank 1 noncoval) an to imprinted polymer of Example 1 (Poly 2 cov) and the corresponding non imprinted polymer (Blank 2 cov). The Experiment followed again the batch binding, this time with variable amount of polymer.

EXAMPLE 6

The polymerisation procedure was carried out as in Example 1. Then a known amount of liquid polymerisation mixture is place on a PTFE membrane (Millipore, Fluoropore FHUP04700), 0.5 microns cutoff and allowed to polymerise (thermic or UV). The resulting polymers show a noticeable difference between specific and nonspecific binding. Results:

imprinted polymer 24.1%
non-imprinted polymer 0%.

These sort of membranes can be used in biosensors as a one-off "dip in" analysis that would give rapid and accurate results.

The polymer on the membranes may be cleaned by a process involving 1 hour cleaning in NaOH in $CH_3OH$ (1M) followed by 30 min extracting in $CH_3oH$ (cold extraction, not Soxhlet) followed by immersion for 5 min in water (strong shaking). The membranes are highly hydrophobic and they maintain this property after being modified. By immersing them in water they will repel the last traces of solvent and will dry very quickly.

EXAMPLE 7

Figure 3:
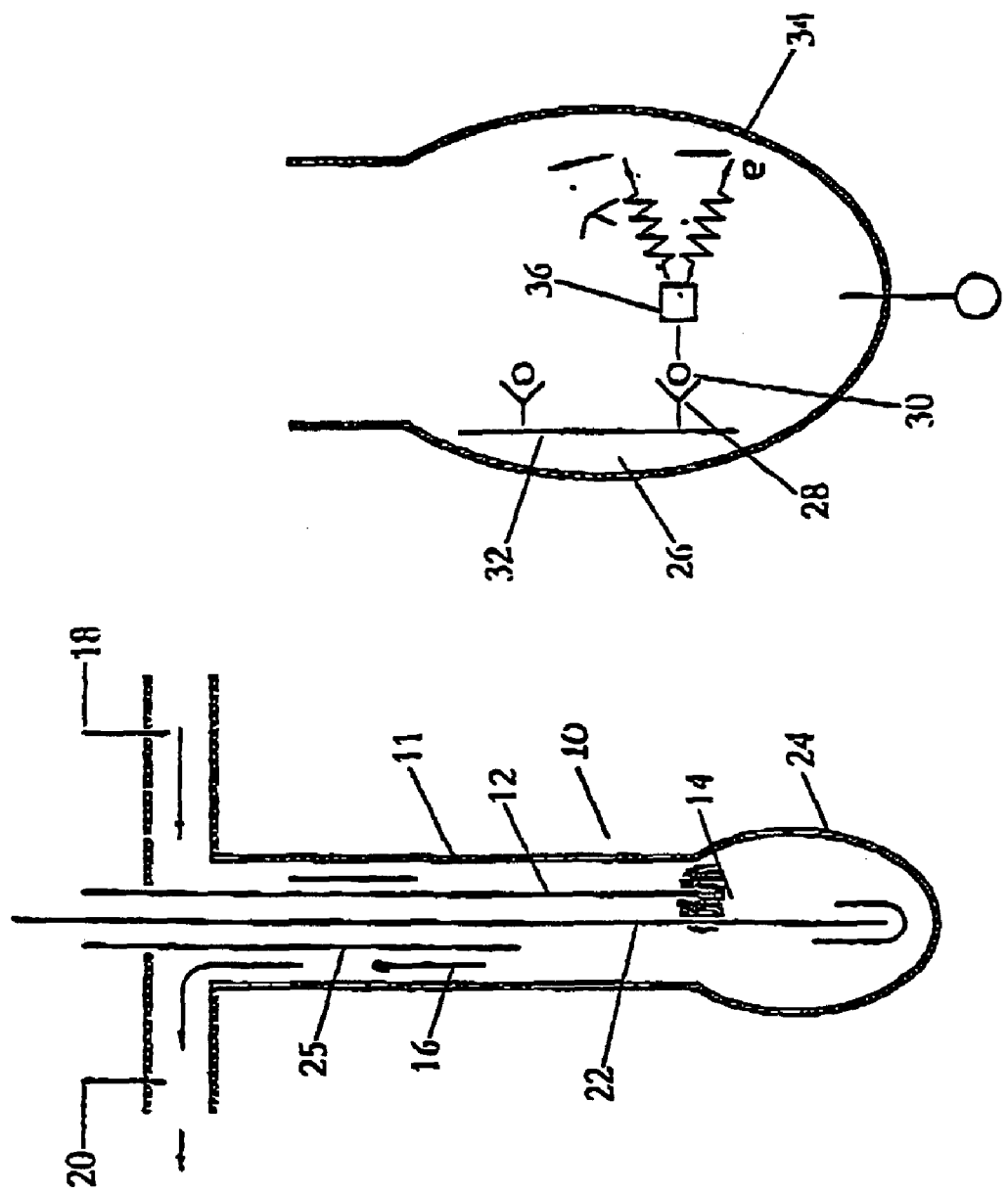
FIG. 3 shows a schematic representation of a probe of the current present invention.

FIG. 3 offers a schematic representation of the probe components as detailed in the present invention. These include an inlet tube (18) that allows introduction of anaesthetic into the probe which can be monitored in numerous forms, including but not exclusively by flow rates by on-line monitoring, a central body (11) of the probe (10) is included, constructed of known materials such as steels, alloys, plastics, glass in a concentric manner and including (24) a selective membrane design that separates the analysis actions within the probe from the sample and/or substrate. Within the central body of the probe lies the sensor components (12, 16, 25) surrounded by, or in contact with, or directed towards propofol imprinted polymer (14).

The internal probe is separated by divider (22) into two chambers until a short distance prior to the actual separation membrane. The probe also consists of an outlet (20) with monitoring opportunities as described for the inlet. This outlet also offers the opportunity for actual sample collection should it be desirable. The sensor arrangement within the probe (12,16,25) can be connected to amplifying, displaying and quantifying devices including the provision for logging of data or radio-electric transmission to a receiver some distance away.

EXAMPLE 8

One probe of the invention depicted in FIGS. 3a and 3b comprises a response portion (26) comprising an area of receptors. These comprise imprinted polymer of the invention specific to propofol (30), bound to a supporting substrate (32). The components are housed in a body (11) allowing fluid from the sample to access the response portion (26). The response portion (26) may be housed in the head of the body (11), while the bulk of equipment associated with evaluating the labeled standard can be positioned other than in the head to reduce its size.

The receptor may comprise imprinted polymer arranged around the base area of the probe in a number of formats. These may include formation of the polymer on the measuring electrode (12), which may be platinum mesh, gold, stainless steel, carbon, alloys or optic fibres coated with imprinted polymer, as a very thin layer or even a monolayer. Other methods of attaching the polymer are not excluded.

A fibre optic (25) delivers exciting electromagnetic radiation from a light source and also delivers emitted fluoresced light from the label of introduced standard at the surface of the response portion (26) to suitable electronic circuitry.

In FIG. 3b it can be seen that in use an anaesthetic of interest (30) in the sample may selectively travel across a membrane (34) into he measurement part of the probe. Once there (30) may bind to an polymer of the invention (28) fixed within the probe. An introduced ligand (36) competitively binds to the same set of receptors (28). This introduced ligand (36) is then activated to produce energy proportional to the number of ligands (36) bound. This energy is monitored, and measured to give a relative measure of (36) bound and therefore (30) bound.

This relative measure is calibrated from the performance of the probe using standards of (36) and (30) in an in vitro calibration or in vivo internal standard test.

According to one method of use, the probe will be calibrated, typically in a sample of pure labeled standard to obtain a 100% reading. Known standards comprising known mixture of both labeled and non-labeled competitively binding substances may be used for calibration, or to obtain various data points for subsequent comparison and analysis. Calibration will normally occur in vitro, before and after use although in vivo calibration using internal standards is also possible. The probe, after washing, will be placed in the sample and allowed to eqilibrate. A standard of labeled substance is introduced to the ample or system being monitored, allowed to distribute and competitively bind at the receptor sites. After equilibration, meaningful data from the sensor portion may be collected and analysed.

By using multiple labels to the single bound antibody it is possible to amplify the measurement potential of the probe to measure very small concentrations of anaesthetic.

EXAMPLE 9

The membranes for use in this Example were prepared as in Example 6. The polymerisation mixture (composed of propofol 4(vinylphenyl) carbonate (monomer) and ethyleneglycolmethacrylate (1:1 molor ratio), 5% initiator (AB-CHC) and toluene (0.5 mL/g monomer+EDMA) was purged with nitrogen for 1 minute, then 200 microlitres were applied on the membrane.

The membrane thus modified was allowed to polymerise for 24 hours, 70 degrees C. The blanks were made following the same recipe, but with no monomer added. The membranes were tested for their ability to bind propofol. Blood was spiked with propofol in known concentrations (between 0 and 10 ppm, increasing in 0.5 ppm steps), vortexed (1000 rpm) for 2 min/vial and allowed to settle (to make sure the propofol binds to proteins and behaves as in test samples). Samples (400 microliters) of blood were mixed with 1.6 mL methanol. The mixture was vortexed (1000 rpm) for 10 seconds to allow total blood precipitation. The mixture of methanol and precipitated blood was passed through a 0.2 microns filter. 1 mL of the filtrate was put in contact with the imprinted membranes, and allowed to stay i contact for 2 min. The solution that the membranes were in was tested by HPLC to assess propofol that was not bound.

The membranes were cleaned in water (just rinsed) to remove unbound propofol and methanol surrounding them.

Propofol was extracted from the membranes by placing them in 400 microliters of mixture (bicarbonate buffer): methanol 1:1 (bicarbonate buffer pH 9.6, 10 mM), in a sealed vial, and sonicated (ultrasound cleaning bath) for 1 min.

The solution was assessed for propofol concentration by either HPLC or colorimetric tests (reaction with Gibbs reagent, and reading of the complex colour at 592 nm).

Gibbs test: 400 microliters of the extract+200 microliters 0.5 nM Gibbs reagent in methanol. A colour forms instantly, varying from yellow to blue depending on the concentration of the propofol released.

Figure 4:
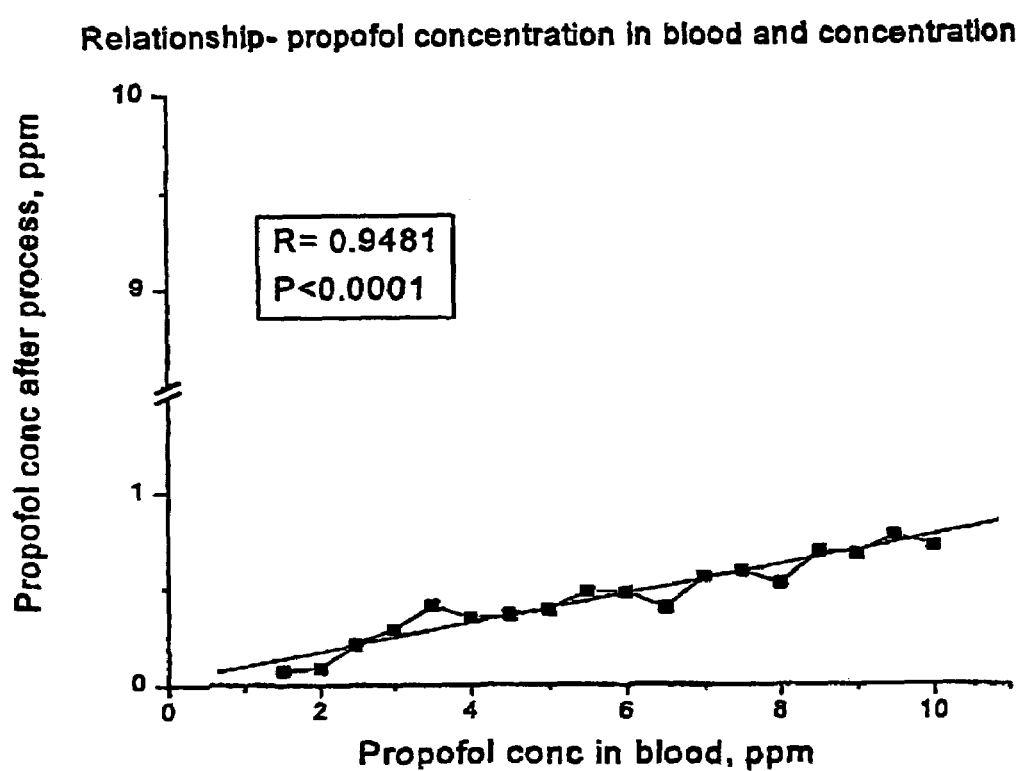
FIG. 4 shows a graph of the relationship of propofol concentration determined using the invention to the propofol concentration in blood.

The results show the propofol concentration measured correlate strongly with the propofol concentrations of the original blood (see FIG. 4).

The membranes used for this test can be put in contact with methanol for a further 30 min (shaking) and then immersed in water for 5 min with strong shaking to repel solvent as described in Example 6 and used for a new test. The system described can use the same membranes for up to 5000 times with no sensitivity loss.

It should be noted that the invention can be carried out with numerous modifications and variations and that the above Examples are by way of illustration only. For example the invention may be carried out using other phenols an the polymers used may be prepared using different monomers and/or proportions and/or corsslinkers.

What we claim is:

1. A method for the detection and/or measurement of a phenol comprising:
   (a) contacting the sample to be tested with a polymer imprinted with the phenol or an analogue thereof;
   (b) measuring binding of the phenol to the polymer.

2. A method as claimed in claim 1 wherein said imprinted polymer was prepared by polymerising a polymerisable monomer, to which a phenol is covalently bound by a hydrolysable linker, and subsequently removing the phenol by hydrolysis.

3. A method as claimed in claim 2 wherein said monomer has the formula MXP wherein;
   P is a (substituted) phenoxy group;
   M is a polymerisable group containing an alkenyl group;
   X is a bond or a linker group susceptible to hydrolysis under conditions which do not result in destruction of the polymer backbone.

4. A method as claimed in claim 3 wherein X or X together with M and/or P contains an —O—CO—O— group.

5. A method as claimed in claim 4 wherein M is a vinylphenyl group, and X and the oxy group of P form an —O—CO—O— group.

6. A method as claimed in claim 1 wherein said imprinted polymer was prepared by preparing or crosslinking a polymer in the presence of the phenol, with subsequent removal of phenol.

7. A method as claimed in claim 6 wherein the polymer is a crosslinked polyacrylate or polymethacrylate.

8. A method as claimed in claim 7 wherein the polymer is a polymethacrylate crosslinked with ethylenedimethacrylate.

9. A method as claimed in claim 1 wherein the particle size of at least 50% (by weight) of the polymer is in the range 0.5–5 microns.

10. A method according to claim 1 wherein the imprinted polymer is formed by placing the polymerisation mixture on a porous polymer membrane and allowing the mixture to polymerise.

11. A method sa claimed in claim 10 wherein the porous polymer membrane is a PTFE membrane.

12. A method as claimed in claim 1 wherein the phenol is substituted with 1 to 3 $C_1$–$C_3$ alkyl groups.

13. A method as claimed in claim 12 where the phenol is substituted with 1 to 3 substituents selected from $C_1$–$C_6$ alkyl, halogen, $C_5$–$C_6$ alkoxy, $C_1$–$C_6$ alkylthio, amino, $C_1$–$C_6$ alkylamino, di($C_1$–$C_3$alkyl) amino, —$CONH_2$, —CN, carboxy, hydroxy, $C_1$–$C_6$ alkylsulfonyl, nitro, and substituted $C_1$–$C_6$ alkoxy or alkoxy wherein the substituent is selected from halogen, hydroxy, $C_1$–$C_3$ alkoxy, amino, —$CONH_2$, —CN and carboxy.

14. A method as claimed in claim 13 wherein the phenol is substituted with 1 to 3 $C_1$–$C_3$ alkyl groups.

15. A sensor for detecting/measure propofol, comprising a probe having an imprinted polymer as defined in claim 1.

16. A method as claimed in claim 15 wherein the phenol is propofol.

17. A sensor for detecting/measure propofol, comprising a probe having an imprinted polymer as defined in any previous claim.

18. An imprinted polymer prepared by polymerising a polymerisable monomer, to which a phenol is covalently bound by a hydrolysable linker, and subsequently removing the phenol by hydrolysis.

19. An imprinted polymer as claimed in claim 18 wherein said monomer has the formula MXP and wherein;
   P is a (substituted) phenoxy group;
   M is a polymerisable group containing an alkenyl group.

20. An imprinted polymer prepared by preparing or crosslinking a polymer in the presence of a phenol substituted with from 1 to 3 $C_1$–$C_6$ alkyl groups and subsequently chemically or physically removing the substituted phenol.

21. An imprinted polymer as claimed in claim 20 wherein the polymer is a crosslinked polyacrylate or polymethacrylate.

22. An imprinted polymer as claimed in claim 21 wherein the polymer is a polymethacrylate crosslinked with ethylenedimethacrylate.

23. An imprinted polymer as claimed in claim 16 wherein the phenol is substituted with 1 to 3 $C_1$–$C_3$ alkyl groups.

24. An imprinted polymer as claimed in claim 23 wherein the phenol is propofol or a cresol.

25. An imprinted polymer as claimed in claim 24 wherein tire phenol is propofol.

* * * * *